United States Patent
Smith

(10) Patent No.: US 10,793,808 B2
(45) Date of Patent: Oct. 6, 2020

(54) POTASSIUM SOAPS THAT CAN BE THICKENED WITH CHLORIDE SALTS

(71) Applicant: Vanguard Soap LLC, Memphis, TN (US)

(72) Inventor: Scott A. Smith, Memphis, TN (US)

(73) Assignee: Vanguard Soap LLC, Memphis, TN (US)

( * ) Notice: Subject to any disclaimer, the term of this patent is extended or adjusted under 35 U.S.C. 154(b) by 0 days.

(21) Appl. No.: 15/197,456

(22) Filed: Jun. 29, 2016

(65) Prior Publication Data

US 2016/0376526 A1    Dec. 29, 2016

Related U.S. Application Data

(60) Provisional application No. 62/186,099, filed on Jun. 29, 2015.

(51) Int. Cl.

| | | |
|---|---|---|
| *C11C 1/00* | (2006.01) | |
| *C11C 1/02* | (2006.01) | |
| *C11D 9/10* | (2006.01) | |
| *C10M 105/24* | (2006.01) | |
| *C10M 169/04* | (2006.01) | |
| *A61K 8/36* | (2006.01) | |
| *A61K 8/20* | (2006.01) | |
| *A61Q 5/02* | (2006.01) | |
| *A61Q 19/10* | (2006.01) | |
| *C11D 13/02* | (2006.01) | |
| *C11D 17/08* | (2006.01) | |
| *C10M 117/02* | (2006.01) | |
| *C10M 117/04* | (2006.01) | |
| *C10M 129/40* | (2006.01) | |
| *C10M 129/44* | (2006.01) | |
| *C10N 10/02* | (2006.01) | |
| *C10N 70/00* | (2006.01) | |

(52) U.S. Cl.
CPC ................ *C11C 1/025* (2013.01); *A61K 8/20* (2013.01); *A61K 8/36* (2013.01); *A61Q 5/02* (2013.01); *A61Q 19/10* (2013.01); *C10M 105/24* (2013.01); *C10M 117/02* (2013.01); *C10M 117/04* (2013.01); *C10M 129/40* (2013.01); *C10M 129/44* (2013.01); *C10M 169/04* (2013.01); *C11D 9/10* (2013.01); *C11D 13/02* (2013.01); *C11D 17/08* (2013.01); *A61K 2800/48* (2013.01); *C10M 2201/081* (2013.01); *C10M 2207/1203* (2013.01); *C10M 2207/125* (2013.01); *C10M 2207/126* (2013.01); *C10M 2207/128* (2013.01); *C10M 2207/1256* (2013.01); *C10M 2207/1265* (2013.01); *C10M 2207/1285* (2013.01); *C10N 2010/02* (2013.01); *C10N 2070/00* (2013.01)

(58) Field of Classification Search
CPC ........... C11C 1/025; C11D 9/10; C11D 13/02; C11D 2201/081; C10M 105/24; C10M 169/04; C10M 2207/1203; C10M 2201/081; C10M 117/02; C10M 117/04; C10M 129/40; C10M 129/44; C10M 2207/125; C10M 2207/1256; C10M 2207/128; C10M 2207/1285; C10N 2210/01; C10N 2270/00; A61K 8/36; A61K 8/20; A61K 2800/48; A61Q 5/02; A61Q 19/10

See application file for complete search history.

(56) References Cited

U.S. PATENT DOCUMENTS 3,846,326 A * 11/1974 Wright .................. A61K 8/345
510/129

FOREIGN PATENT DOCUMENTS

| FR | 1457935 | * 11/1966 |
|---|---|---|
| GB | 1059089 | * 2/1967 |

OTHER PUBLICATIONS http://www.lovinsoap.com/2010/09/liquid-soap-neutralizing-and-superfating/.*

* cited by examiner

*Primary Examiner* — Cephia D Toomer
(74) *Attorney, Agent, or Firm* — Butler Snow LLP

(57) ABSTRACT

Natural liquid potassium soap compositions and methods of manufacturing and using the same are provided with thickening by the addition of chloride salts, such as sodium chloride and potassium chloride. The natural liquid potassium soap compositions may contain one or more fatty acids with carbon length ranging from four (C4) to twenty-two (C22) or natural fatty acid mixtures with coconut oil, olive oil, tallow, sunflower oil, safflower oil, and/or tall oil fatty acids which are saponified with lye. The saponification lye is preferably potassium hydroxide. Preferred embodiments contain potassium salts of fatty acids comprising at least oleic acid (C18:1 cis-9), olive oils, coconut oils or mixtures thereof. The chloride salt is added in either solid or liquid form following saponification and neutralization.

13 Claims, No Drawings

POTASSIUM SOAPS THAT CAN BE THICKENED WITH CHLORIDE SALTS

CROSS-REFERENCE TO RELATED APPLICATIONS

This application claims priority to U.S. Provisional Application No. 62/186,099 to Scott A. Smith filed on Jun. 29, 2015, the contents of which are incorporated herein by reference in its entirety.

FIELD OF THE INVENTION

The present invention is generally directed towards natural liquid soap compositions that can be thickened with chloride salts and methods for manufacturing thickened natural soap compositions made from various carbon chain length fatty acids.

BACKGROUND OF THE INVENTION

Soap can be defined as a salt of one or more of the higher fatty acids with an alkali or metal. Most soaps are made by the action of potassium or sodium hydroxide on animal fats and vegetable oils (or fatty acids). The preparation of soap directly from the raw fatty acids by the use of a lye (either potassium or sodium hydroxide) is referred to as saponification, which is well known in the art of soap manufacture.

Commercial potassium soaps generally have low viscosities, a harsh after-feel, and are not able to achieve viscosity build characteristics with the addition of chloride salts. Products currently sold in the market place are typically thickened with cellulosic (such as hydroxyethyl cellulose or HEC) or polymeric thickeners if not just left in their natural low viscosity ("watery") state. Such thickened commercial potassium soaps are found in numerous products used as general cleaning soaps, shampoos, body washes, etc.

There is a need for soap made with all natural products that can maintain a luxurious feel through proper fatty acid and natural oil selection as well as their ability to be thickened with chloride salts without separating, losing their raised viscosity, and clarity.

SUMMARY OF THE INVENTION

Accordingly, it is an object of the present invention to provide novel natural liquid soap compositions and methods that overcome these and other problems of the prior art by providing natural liquid soap compositions thickened with chloride salts that can maintain a luxurious feel through proper fatty acid and natural oil selection as well as their ability to not lose their raised viscosity and clarity. In one aspect, the present invention provides a method of manufacturing of a natural liquid soap composition comprising the step of saponifying one or more fatty acids ranging in carbon length from four (C4) to twenty-two (C22). In some embodiments, the fatty acids comprise a mixture of fatty acids ranging in carbon length from four (C4) to twenty-two (C22). In some embodiments, natural fatty acid mixtures with coconut oil, olive oil, tallow, sunflower oil, safflower oil, and/or tall oil fatty acids are used. In some preferred embodiments, the fatty acids comprise at least oleic acid (C18:1 cis-9). In other preferred embodiments, the fatty acids comprise at least olive oils. In other preferred embodiments, the fatty acids comprise at least coconut oils. In still other preferred embodiments, the fatty acids comprise at least oleic acid (C18:1 cis-9), olive oils, coconut oils or mixtures thereof. The step of saponification may be performed by adding lye in some embodiments. In preferred embodiments, the lye is potassium hydroxide. For thickening, chloride salts are added following saponification and neutralization and may be added to the reaction vessel in solid or solution form. Preferably, the chloride salts are selected from either sodium chloride or potassium chloride or combinations thereof.

In another aspect, the present invention provides a natural liquid soap composition comprising one or more saponified fatty acids ranging in carbon length from four (C4) to twenty-two (C22). In some embodiments, the fatty acids comprise a mixture of fatty acids ranging in carbon length from four (C4) to twenty-two (C22). In some embodiments, natural fatty acid mixtures with coconut oil, olive oil, tallow, sunflower oil, safflower oil, and/or tall oil fatty acids are used. In some preferred embodiments, the fatty acids comprise at least oleic acid (C18:1 cis-9). In other preferred embodiments, the fatty acids comprise at least olive oils. In other preferred embodiments, the fatty acids comprise at least coconut oils. In still other preferred embodiments, the fatty acids comprise at least oleic acid (C18:1 cis-9), olive oils, coconut oils or mixtures thereof. In preferred embodiments, the saponified fatty acids are prepared with potassium hydroxide. The natural liquid soap composition is thickened with a chloride salt, which may be added to the reaction vessel in solid or solution form. Preferably, the chloride salt is selected from either sodium chloride or potassium chloride or combinations thereof.

In another aspect, the present invention provides a natural liquid soap composition in various administration forms, such as soaps (liquid or foaming cleansers), wipes, shampoos, lotions, body/bath soap gels, exfoliate cleansers, and industrial soaps and lubricants comprising one or more saponified fatty acids ranging in carbon length from four (C4) to twenty-two (C22). In some embodiments, the fatty acids comprise a mixture of fatty acids ranging in carbon length from four (C4) to twenty-two (C22). In some embodiments, natural fatty acid mixtures with coconut oil, olive oil, tallow, sunflower oil, safflower oil, and/or tall oil fatty acids are used. In some preferred embodiments, the fatty acids comprise at least oleic acid (C18:1 cis-9). In other preferred embodiments, the fatty acids comprise at least olive oils. In other preferred embodiments, the fatty acids comprise at least coconut oils. In still other preferred embodiments, the fatty acids comprise at least oleic acid (C18:1 cis-9), olive oils, coconut oils or mixtures thereof. In preferred embodiments, the saponified fatty acids are prepared with potassium hydroxide. The natural liquid soap composition is thickened with a chloride salt, which may be added to the reaction vessel in solid or solution form. Preferably, the chloride salt is selected from either sodium chloride or potassium chloride or combinations thereof.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The present invention provides a series of novel natural liquid potassium soap compositions thickened with chloride salts and methods making the same that overcome the problems of the prior art discussed above, as well as other problems. While the embodiments are discussed herein as being directed toward natural liquid potassium soap compositions and related methods, a person of skill in the art would appreciate that the present invention's natural liquid potassium soap compositions and related methods can be used or as a base of a soap composition to treat and prevent a variety of microbial infections (or, for example, prevention of microbial contamination) by cleansing or treating the skin and/or hair of a subject in need thereof. For example, a subject in need thereof can be an animal with exposure to or susceptibility to a microbial infection or transfer on or from its skin and/or hair (fur). In preferred embodiments, a subject in need thereof is a person with an exposure to or susceptibility to a microbial infection on the skin or a general need to cleanse the subject's skin of microbial flora. Furthermore, a person of skill in the art would appreciate that the present invention's natural liquid potassium soap compositions and related methods can be used alone or as a base of a soap composition comprising an industrial/commercial cleaning agent, an anti-microbial surface cleanser, a bath or hand soap/gel, a shampoo, and skin care lotions and creams.

Thus, in one aspect, the present invention provides a method of manufacturing a natural liquid potassium soap composition comprising the step of saponifying one or more fatty acids ranging in carbon length from four (C4) to twenty-two (C22). In some embodiments, the fatty acids comprise a mixture of fatty acids ranging in carbon length from four (C4) to twenty-two (C22). In some embodiments, natural fatty acid mixtures with coconut oil, olive oil, tallow, sunflower oil, safflower oil, and/or tall oil fatty acids are used. In some preferred embodiments, the fatty acids comprise at least oleic acid (C18:1 cis-9). In other preferred embodiments, the fatty acids comprise at least olive oils. In other preferred embodiments, the fatty acids comprise at least coconut oils. In still other preferred embodiments, the fatty acids comprise at least oleic acid (C18:1 cis-9), olive oils, coconut oils or mixtures thereof. The step of saponification may be performed by adding lye. Any saponifying counter ion can be used in some embodiments. In preferred embodiments, the lye is potassium hydroxide. A thickening step is then performed by adding an appropriate amount of a chloride salt, which may be added to the reaction vessel in solid or solution form. Preferably, the chloride salt is selected from either sodium chloride or potassium chloride or combinations thereof. An appropriate amount is such an amount that results in thickening of the natural liquid potassium soap composition without affecting clarity, color, or cause the soap composition to separate or become less viscous after step completion. The saponified fatty acids (soap) are generally foaming water soluble natural liquid potassium soap compositions that are mild to the skin and have excellent color, clarity, and odor. The natural liquid potassium soap compositions exemplified herein are particularly suited for personal care applications like hand washes, body washes, shampoos, and bubble baths. They are also excellent additives for pet care products, hard surface cleaners, and industrial lubrication applications. They may then be processed with other soaps, pigments, detergents, and/or adjuvants/fragrances that are well known in the field or other processing for preparing commercial soaps, shampoos, wipes, lotions, body/bath soap gels, exfoliate cleansers, or creams for use by a subject in need thereof to create a further natural liquid potassium soap composition of the invention.

In another aspect, the present invention provides a natural liquid potassium soap composition comprising one or more saponified fatty acids ranging in carbon length from four (C4) to twenty-two (C22). In some embodiments, the fatty acids comprise a mixture of fatty acids ranging in carbon length from four (C4) to twenty-two (C22). In some embodiments, natural fatty acid mixtures with coconut oil, olive oil, tallow, sunflower oil, safflower oil, and/or tall oil fatty acids are used. In some preferred embodiments, the fatty acids comprise at least oleic acid (C18:1 cis-9). In other preferred embodiments, the fatty acids comprise at least olive oils. In other preferred embodiments, the fatty acids comprise at least coconut oils. In still other preferred embodiments, the fatty acids comprise at least oleic acid (C18:1 cis-9), olive oils, coconut oils, or mixtures thereof. The fatty acids ranging in carbon length from four (C4) to twenty-two (C22) or natural fatty acid mixtures with coconut oil, olive oil, tallow, sunflower oil, safflower oil, and/or tall oil fatty acids are saponified by addition of a lye or other appropriate potassium counter ion to create the saponified fatty acids. In some preferred embodiments, the saponified fatty acids are prepared with potassium hydroxide as the lye. In some preferred embodiments, the fatty acids comprise at least oleic acid (C18:1 cis-9). In other preferred embodiments, the fatty acids comprise at least olive oils. In other preferred embodiments, the fatty acids comprise at least coconut oils. In still other preferred embodiments, the fatty acids comprise at least oleic acid (C18:1 cis-9), olive oils, coconut oils, or mixtures thereof. In my practice, the type and source of olive oil has caused no significant difference (other than color) in a process batch.

I have surprisingly found that substituting at least a portion of coconut oil in process batches with natural unsaturated fatty acids, such as, but not limited to, oleic acid, ricinoleic fatty acid, eurucic fatty acid, olive oils, sunflower oils, and/or safflower oils, allows for a lower requirement for percent solids in a potassium fatty acid soap while maintaining effective cleaning ability. However, I have also found that high saturated fatty acid components, such as coconut oil, is needed to efficiently complete saponification reactions that also contain oleic acid (including unsaturated fatty acids and oils, such as, but not limited to, olive oil). Having too much oleic acid (unsaturated fatty acids/oils) in the reaction can force the reaction to break and resort in high residual oils due to incomplete saponification. A person of skill in the art can follow the disclosure herein to determine the best ratio of coconut oils (saturated) to oleic acid (unsaturated) that maintains efficient completion of saponification and maintains the texture and viscosity required for the intended application The natural liquid potassium soap compositions are thickened with an appropriate amount of chloride, such as a chloride salt, which may be added to the reaction vessel in solid or solution form. Preferably, the chloride salt is selected from sodium chloride and potassium chloride, or combinations thereof. An appropriate amount is such an amount that results in thickening of the soap composition without affecting clarity, color, or cause the soap composition to separate or become less viscous after step completion. The reaction can be monitored by a person of skill in the art to achieve this. I have surprisingly found that the thickening of the soap compositions with chloride allows for lower percent solids while maintaining cleaning effectiveness and desirable viscosity in a broad range of liquid soap applications. I have also surprisingly found that combining the chloride additive with a substitution of coconut oil (predominantly saturated fatty acids) with oleic acid (predominantly unsaturated fatty acid) has a synergistic effect on the requirements for percent solids in a liquid soap composition while maintaining cleaning effectiveness and desirable viscosity in a broad range of liquid soap applications. For example, as little as 4-7% (weight) of added sodium chloride to a reaction batch will achieve high viscosity in many natural fatty acid or combination natural fatty acids soap compositions.

A person of skill in the art will be able to monitor a batch reaction during the addition of chloride to achieve the desired viscosity for the intended application of that soap composition batch. It is also understood that depending on the intended final application for the natural potassium soap composition, the desired viscosity will vary. For example, some liquid saponified fatty acids (soap) described herein are generally foaming water soluble natural soap compositions that are mild to the skin and have excellent color, clarity, and odor. A viscosity value of about 2,000 cPs at room temperature is generally acceptable for a hand soap. However, a body wash may be desired to be around 12,000 cPs at room temperature for customer acceptance. Also, body wash gels and shampoos may similarly need to be within 12,000 and 40,000 cPs at room temperature. An abrasive or exfoliate liquid soap product will be more desirable to the consuming public if it has the consistency of a gel, which is about 40,000 cPs at room temperature. Decreased percent solids in the final consumer product allows for processing batches as liquid soap concentrates that can be further diluted by water to achieve the desired final viscosity for different applications. This discovery has led to decreased processing time and wear on reaction vessels, as well as decreased costs per unit of final soap product, among other benefits over the prior art.

The natural liquid potassium soap compositions exemplified herein are particularly suited for personal care application like hand washes, body washes, shampoos, and bubble baths. They are also excellent additives for pet care products, hard surface cleaners, and industrial lubrication applications. They may then be processed with other soaps, detergents, pigments, and/or adjuvants/fragrances that are well known in the field or other processing for preparing commercial soaps, shampoos, wipes, lotions, body/bath soap gels, exfoliate cleansers, or creams for use by a subject in need thereof to create a further natural liquid potassium soap composition of the invention.

Example 1

Method of Manufacture

Manufacturing natural liquid potassium soap compositions that are thickened with chloride salts has proven difficult to achieve in a consistent clear particulate free form. Most commercial products are therefore thickened with HEC (hydroxyethyl cellulose) or polymeric compounds. The following example provides the general procedure used to achieve consistent clear particulate free form for natural liquid potassium soap compositions that are thickened with chloride salts. To a reaction flask equipped with agitation, heat, thermometer, and nitrogen sparge is added the specified amount of fatty acid and or natural oil(s). Next the specified mass (e.g., number of grams) of potassium hydroxide reactant is added under good agitation with and without a nitrogen sparge. Sodium hydroxide can be used in lieu of or in mixtures with potassium hydroxide, which will require different specified mass based on the mass difference between sodium and potassium. However, potassium hydroxide is preferred for liquid soap concentrates and applications. Next is added enough water to make the final product have a solids content of 30-60% by weight, depending on the application or concentrate being prepared. This can be determined by monitoring the reaction as water is added. Nitrogen sparge, when utilized, is simply nitrogen gas bubbled through the liquid contents of the flask at a rate low enough not to produce too much foam and a rate high enough to keep the color light by minimizing oxidation. While nitrogen sparge is not required in the method, it is advantageous to use in reactions containing base oils or fatty acids of carbon chain length having a susceptibility to oxidation in order to prevent color bodies from building. The reaction mass is heated to 90-105° C. and is held for 2-5 hours.

Testing for the %-free alkali follows the reaction progress. Once the theoretical value is reached, the reaction is terminated. When the reaction is terminated, the free alkalinity is then neutralized to an acceptable pH and/or alkalinity range with an acceptable neutralizing agent. For the purpose of these examples hydrochloric acid and/or citric acid were utilized for neutralization; however, those skilled in the art may use other neutralizing agents without departing from the spirit and scope of the invention. A person of ordinary skill in the art will understand that an acceptable pH and/or alkalinity range may depend on the intended use of the final product (e.g., hand soap, antiseptic cleaning soap, shampoo, bath gel, etc.) with most having an alkaline pH. All simple and blended sample compositions were tested over a range of pH from 8.8 to 13.5, with the optimum range being from 9.5 to 10.2 for liquid soap applications. Upon neutralization to an acceptable pH and/or alkalinity, an appropriate amount of a chloride salt is added to thicken the composition. The chloride salt may be added to the reaction vessel in solid or solution form. Preferably, the chloride salt is selected from either sodium chloride or potassium chloride or combinations thereof. Preferably, the product is used without additional purification or processing. With each Sample (see TABLE 1), multiple simple and blended compositions of the fatty acids/oils below were assembled to achieve optimization for different applications. The percent solids were tested at a range of 18.0% (weight) to 75% (weight), with the optimum being in the range of 38.5% (weight) to 41.5% (weight) for liquid soap applications. As described further below, the batches (especially those with a range around 40% solids, but not limited to these) may be produced as a liquid soap concentrate that may be further diluted with water to achieve a final consumer liquid soap product having 20% or less percent solids. Alternatively, the concentrated formulations may be packaged and sold to consumers as concentrated potassium soap compositions, which also generates costs savings in decreased packaging and shipping costs, as well as decreased shelving/storage needed by retailers.

TABLE 1

| Sample | Fatty Acid and or Oil Name | Carbon Chain |
| --- | --- | --- |
| 1 | Butyric/Caproic | C4/C6 |
| 2 | Caprylic | C8 |

TABLE 1-continued

| Sample | Fatty Acid and or Oil Name | Carbon Chain |
|---|---|---|
| 3 | Capric | C10 |
| 4 | Caprylic/Capric | C8/C10 |
| 5 | Lauric | C12 |
| 6 | Myristic | C14 |
| 7 | Lauric/Myristic | C12/C14 |
| 8 | Palmitic | C16 |
| 9 | Stearic | C18 |
| 10 | Oleic | C18:1 |
| 11 | Ricinoleic | C18:1(OH) |
| 12 | Behenic/Eurucic | C22/C22:1 |
| 13 | Coconut Oil | Whole Oil Distribution |
| 14 | Olive Oil | Whole Oil Distribution |
| 15 | Tall Oil Fatty Acid | Whole Oil Distribution |

Example 2

Butyric and Caproic Acid Sample Formulation

A sample composition including both butyric fatty acid (C4) and caproic fatty acid (C6) according to the teachings above was prepared. The composition comprised about 12.6% (weight) butyric fatty acid and about 17.9% (weight) caproic fatty acid. Potassium hydroxide was included at about 10.4% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of deodorizing and disinfecting hard surfaces, skin, and hair (fur) with low foam. Also, heavy duty cleaning applications for metal surfaces and other industrial surfaces.

Example 3

Caprylic and/or Capric Acid Sample Formulation 1

A sample composition including either or both caprylic fatty acid (C8) and capric fatty acid (C10) according to the teachings above was prepared. The composition comprised about 30.5% (weight) total of caprylic fatty acid and/or capric fatty acid. Potassium hydroxide was included at about 10.4% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of deodorizing and disinfecting hard surfaces, skin, and hair (fur) with low foam. Also, heavy duty cleaning applications for metal surfaces and other industrial surfaces.

Example 4

Caprylic and Capric Acid Sample Formulation 2

A sample composition including both caprylic fatty acid (C8) and capric fatty acid (C10) according to the teachings above was prepared. The composition comprised about 12% to about 15% (weight) of caprylic fatty acid and about 12% to about 15% (weight) of capric fatty acid. Potassium hydroxide was included at about 10.4% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of deodorizing and disinfecting hard surfaces, skin, and hair (fur) with low foam. Also, heavy duty cleaning applications for metal surfaces and other industrial surfaces.

Example 5

Lauric Acid Sample Formulation

A sample composition including lauric fatty acid (C12) according to the teachings above was prepared. The composition comprised about 28.8% (weight) of lauric fatty acid. Potassium hydroxide was included at about 11.2% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable.

Example 6

Lauric Acid and Myristic Acid Sample Formulation

A sample composition including both lauric fatty acid (C12) and myristic fatty acid (C14) according to the teachings above was prepared. The composition comprised about 20% (weight) of lauric fatty acid and about 8.8% (weight) of myristic fatty acid. Potassium hydroxide was included at about 11.4% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable.

Example 7

Myristic Acid Sample Formulation

A sample composition including myristic fatty acid (C14) according to the teachings above was prepared. The composition comprised about 30% (weight) of myristic fatty acid. Potassium hydroxide was included at about 11.4% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable.

Example 8

Palmitic Acid Sample Formulation

A sample composition including palmitic fatty acid (C16) according to the teachings above was prepared. The composition comprised about 30.2% (weight) of palmitic fatty acid. Potassium hydroxide was included at about 10.4% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable.

Example 9

Palmitic Acid and Stearic Acid Sample Formulation

A sample composition including both palmitic fatty acid (C16) and stearic fatty acid (C18) according to the teachings above was prepared. The composition comprised about 20.5% (weight) of palmitic fatty acid and about 10% (weight) of stearic fatty acid. Potassium hydroxide was included at about 10.8% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable.

Example 10

Oleic Acid and Stearic Acid Sample Formulation

A sample composition including both oleic fatty acid (C18:1; omega-9) and stearic fatty acid (C18) according to the teachings above was prepared. The composition comprised about 20% (weight) of oleic fatty acid and about 11% (weight) of stearic fatty acid. Potassium hydroxide was included at about 11% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable.

Example 11

Oleic Acid and Olive Oil Sample Formulation

A sample composition including both oleic fatty acid (C18:1; omega-9) and olive oil (whole oil distribution of constituent oils, which will naturally vary by lot and source) according to the teachings above was prepared. The composition comprised about 24% (weight) of oleic fatty acid and about 4% (weight) of olive oil. Potassium hydroxide was included at about 9.8% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable.

Example 12

Coconut Oil, Oleic Acid, and Olive Oil Sample Formulation

A sample composition including coconut oil (whole oil distribution of constituent oils, which will naturally vary by lot and source), oleic fatty acid (C18:1; omega-9), and olive oil (whole oil distribution of constituent oils, which will naturally vary by lot and source) according to the teachings above was prepared. The composition comprised about 14% (weight) of coconut oil, about 10% (weight) of oleic fatty acid, and about 2% (weight) of olive oil. Potassium hydroxide was included at about 9.8% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 12 (or modified versions that comprise less coconut oil and more oleic fatty acid) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 13

Myristic Acid and Coconut Oil Sample Formulation

A sample composition including both myristic fatty acid (C14) and coconut oil (whole oil distribution of constituent oils, which will naturally vary by lot and source) according to the teachings above was prepared. The composition comprised about 20% (weight) of myristic fatty acid and about 12% (weight) of coconut oil. Potassium hydroxide was included at about 11.8% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 13 (or modified versions that substitute at least some coconut oil for oleic fatty acid) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 14

Coconut Oil and Ricinoleic Acid Sample Formulation

A sample composition including both coconut oil (whole oil distribution of constituent oils, which will naturally vary by lot and source) and ricinoleic fatty acid (C18:1, OH; omega-9) according to the teachings above was prepared. The composition comprised about 14% (weight) of coconut oil and about 14% (weight) of ricinoleic fatty acid. Potassium hydroxide was included at about 9.8% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 14 (or modified versions that comprise less coconut oil and more ricinoleic fatty acid or substituted with at least some oleic fatty acid) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 15

Coconut Oil, Ricinoleic Acid, and Behenic/Eurucic Fatty Acids Sample Formulation A sample composition including coconut oil (whole oil distribution of constituent oils, which will naturally vary by lot and source), ricinoleic fatty acid (C18:1, OH; omega-9), and behenic (C22) and/or eurucic/erucic (C22:1; omega-9) fatty acids according to the teachings above was prepared. The choice of individual or ratio of behenic fatty acid to eurucic fatty acid will depend on the intended final product application or desired viscosity. The composition comprised about 10% (weight) of coconut oil, about 10% (weight) of ricinoleic fatty acid, and about 8% (weight) total of behenic and/or eurucic/erucic fatty acids. Potassium hydroxide was included at about 10% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where low to moderate foam is desirable, as well as skin care and conditioning applications. For some applications, batches following this general formula of Example 15 (or modified versions that comprise less coconut oil and more ricinoleic fatty acid and/or eurucic fatty acid) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 16

Coconut Oil and Olive Oil Sample Formulation

A sample composition including both coconut oil (whole oil distribution of constituent oils, which will naturally vary by lot and source) and olive oil (whole oil distribution of constituent oils, which will naturally vary by lot and source) according to the teachings above was prepared. The composition comprised about 24% (weight) of coconut oil and about 5% (weight) of olive oil. Potassium hydroxide was included at about 11% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 16 (or modified versions that substitute at least some coconut oil for oleic fatty acid and/or more olive oil, which typically contains oleic and linoleic fatty acids as a majority fraction) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 17

Coconut Oil and Tall Oil Fatty Acids Sample Formulation

A sample composition including both coconut oil (whole oil distribution of constituent oils, which will naturally vary by lot and source) and tall oil fatty acids (whole oil distribution of constituent oils, which will naturally vary by lot and source) according to the teachings above was prepared. The composition comprised about 24% (weight) of coconut oil and about 5% (weight) of tall oil fatty acids. Potassium hydroxide was included at about 11% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 17 (or modified versions that substitute at least some coconut oil for oleic fatty acid) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 18

Coconut Oil and Tallow Sample Formulation 1

A sample composition including both coconut oil (whole oil distribution of constituent oils, which will naturally vary by lot and source) and tallow (whole oil distribution of constituent oils, which will naturally vary by lot and source) according to the teachings above was prepared. The composition comprised about 24% (weight) of coconut oil and about 5% (weight) of tallow. Potassium hydroxide was included at about 11% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 18 (or modified versions that substitute at least some coconut oil for oleic fatty) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 19

Coconut Oil and Tallow Sample Formulation 2

A sample composition including both coconut oil (whole oil distribution of constituent oils, which will naturally vary by lot and source) and tallow (whole oil distribution of constituent oils, which will naturally vary by lot and source) according to the teachings above was prepared. The composition comprised about 20% (weight) of coconut oil and about 9% (weight) of tallow. Potassium hydroxide was included at about 11% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 19 (or modified versions that substitute at least some coconut oil for oleic fatty acid) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 20

Coconut Oil Sample Formulation

A sample composition including coconut oil only (whole oil distribution of constituent oils, which will naturally vary by lot and source) according to the teachings above was prepared. The composition comprised about 29% (weight) of coconut oil. Potassium hydroxide was included at about 11% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 20 (or, preferably, modified versions that substitute at least some coconut oil for oleic fatty acid) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 21

Sunflower Oil and Coconut Oil Sample Formulation

A sample composition including both sunflower oil (whole oil distribution of constituent oils, which will naturally vary by lot and source) and coconut oil (whole oil distribution of constituent oils, which will naturally vary by lot and source) according to the teachings above was prepared. The composition comprised about 24% (weight) of sunflower oil and about 5% (weight) of coconut oil. Potassium hydroxide was included at about 12% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 21 (or modified versions that substitute at least some coconut oil for oleic fatty acid or more sunflower oil) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 22

Safflower Oil and Coconut Oil Sample Formulation

A sample composition including both safflower oil (whole oil distribution of constituent oils, which will naturally vary by lot and source) and coconut oil (whole oil distribution of constituent oils, which will naturally vary by lot and source) according to the teachings above was prepared. The composition comprised about 24% (weight) of safflower oil and about 5% (weight) of coconut oil. Potassium hydroxide was included at about 12% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 22 (or modified versions that substitute at least some coconut oil for oleic fatty acid or more safflower oil) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 23

Sunflower Oil, Coconut Oil, and Olive Oil Sample Formulation

A sample composition including sunflower oil (whole oil distribution of constituent oils, which will naturally vary by lot and source), coconut oil (whole oil distribution of constituent oils, which will naturally vary by lot and source), and olive oil (whole oil distribution of constituent oils, which will naturally vary by lot and source) according to the teachings above was prepared. The composition comprised about 20% (weight) of sunflower oil, about 5% (weight) of coconut oil, and about 4% (weight) of olive oil. Potassium hydroxide was included at about 12% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 23 (or modified versions that substitute at least some coconut oil for oleic fatty acid or more olive and/or sunflower oil) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

Example 24

Safflower Oil, Coconut Oil, and Olive Oil Sample Formulation

A sample composition including safflower oil (whole oil distribution of constituent oils, which will naturally vary by lot and source), coconut oil (whole oil distribution of constituent oils, which will naturally vary by lot and source), and olive oil (whole oil distribution of constituent oils, which will naturally vary by lot and source) according to the teachings above was prepared. The composition comprised about 20% (weight) of safflower oil, about 5% (weight) of coconut oil, and about 4% (weight) of olive oil. Potassium hydroxide was included at about 12% (weight). The remaining material in the batch was mostly water. Sufficient citric acid (citrate) was added to neutralize the pH to an acceptable level as discussed above. Also, less than 4% (weight) of sodium chloride was added to increase the viscosity to a desired level. Compositions following this general formulation (with and without modifications) can be used in applications of general cleansing and washing where high foam is desirable. For some applications, batches following this general formula of Example 24 (or modified versions that substitute at least some coconut oil for oleic fatty acid or more olive and/or safflower oil) can be processed as a concentrated liquid soap composition while maintaining desired viscosity (controlled by percent weight of chloride addition) for the final product application. The concentrates can be diluted with water to about 20% (weight) solids with no appreciable loss in cleaning effectiveness or packaged as "green" concentrate products.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

What is claimed:

1. A soap composition consisting essentially of:
   a. one or more fatty acids with a carbon chain length of C4 to C22;
   b. one or more natural oils selected from the group consisting of coconut oil, olive oil, sunflower oil, safflower oil, wherein the one or more natural oils is combined with the one or more fatty acids;
   c. a lye selected from the group of potassium hydroxide, sodium hydroxide, or combinations thereof, wherein the one or more fatty acids and one or more natural oils are saponified with the lye;
   d. and a chloride salt at a weight of 7% or less selected from the group consisting of dry sodium chloride, aqueous sodium chloride solution, dry potassium chloride, aqueous potassium chloride solution, and combinations thereof, wherein the chloride salt is added to the saponified fatty acids after a neutralizing process and does not affect clarity or color, or cause the soap composition to separate or become less viscous.

2. A method of manufacturing the soap composition of claim 1 consisting of saponifying the one or more fatty acids with a carbon chain length of C4 to C22 and one or more natural oils, neutralizing the saponification reaction to an acceptable level of pH, and adding chloride, wherein the saponified fatty acids and natural oils comprise omega-9 unsaturated fatty acids.

3. The method of claim 2, wherein the fatty acids comprise natural oils selected from the group consisting of coconut oil, olive oil, tallow, tall oil fatty acids, sunflower oil, safflower oil, and combinations thereof.

4. The method of claim 2, wherein the fatty acids comprise omega-9 unsaturated fatty acids selected from the group of oleic acid, ricinoleic acid, and eurucic acid, and combinations thereof.

5. The method of claim 2, wherein the one or more fatty acids and one or more natural oils comprise coconut oil and oleic acid.

6. The method of claim 2, wherein the natural oils comprise coconut oil and olive oil.

7. The method of claim 2, wherein the step of saponification comprises reacting the fatty acids with lye.

8. The method of claim 7, wherein the lye is potassium hydroxide.

9. The method of claim 2, wherein the acceptable level of pH is between about 8.8 and about 13.5.

10. The method of claim 9, wherein the acceptable level of pH is between about 9.5 and about 10.2.

11. The method of claim 2, wherein the chloride is a chloride salt selected from the group consisting of dry sodium chloride, aqueous sodium chloride solution, dry potassium chloride, aqueous potassium chloride solution, and combinations thereof.

12. The method of claim 2 further comprising diluting the soap composition with water.

13. The method of claim 2, wherein the step of neutralization comprises adding a neutralizing agent comprising hydrochloric acid, citric acid, or combinations thereof.

\* \* \* \* \*